US012734316B2

(12) United States Patent
White

(10) Patent No.: US 12,734,316 B2
(45) Date of Patent: Sep. 15, 2026

(54) SYSTEM AND METHOD FOR CONTROLLING INHALER DOSAGE

(71) Applicant: RESMED PTY LTD, Bella Vista (AU)

(72) Inventor: Hadley White, Bella Vista (AU)

(73) Assignee: ResMed Pty Ltd, Bella Vista (AU)

( * ) Notice: Subject to any disclaimer, the term of this patent is extended or adjusted under 35 U.S.C. 154(b) by 920 days.

(21) Appl. No.: 17/623,529

(22) PCT Filed: Jun. 27, 2020

(86) PCT No.: PCT/IB2020/056099
§ 371 (c)(1),
(2) Date: Dec. 28, 2021

(87) PCT Pub. No.: WO2020/261232
PCT Pub. Date: Dec. 30, 2020

(65) Prior Publication Data

US 2022/0362493 A1 Nov. 17, 2022

Related U.S. Application Data

(60) Provisional application No. 62/868,300, filed on Jun. 28, 2019.

(51) Int. Cl.
*A61M 15/00* (2006.01)
*A61B 5/00* (2006.01)
(Continued)

(52) U.S. Cl.
CPC ....... *A61M 15/0066* (2014.02); *A61B 5/0205* (2013.01); *A61B 5/082* (2013.01);
(Continued)

(58) Field of Classification Search
CPC ............ A61M 15/0066; A61M 15/009; A61M 2230/202; A61M 2016/0027;
(Continued)

(56) References Cited

U.S. PATENT DOCUMENTS 5,363,857 A * 11/1994 Howard ................. A61B 5/083
600/531
6,958,691 B1 * 10/2005 Anderson ........... A61M 15/008
128/200.14
(Continued)

FOREIGN PATENT DOCUMENTS

CN 101961516 A 2/2011
CN 104582774 A 4/2015
(Continued)

OTHER PUBLICATIONS

International Search Report in International Patent Application No. PCT/IB2020/056099 mailed Aug. 14, 2020 (13 pp.).
(Continued)

*Primary Examiner* — Timothy A Stanis
(74) *Attorney, Agent, or Firm* — NIXON PEABODY LLP

(57) ABSTRACT

A system and method for measuring the effectiveness of a dose from an inhaler on a user. The inhaler includes a drug container and a dosing mechanism coupled to the drug container to aerate a dose from the drug container. The dosing mechanism provides the aerated dose to the user. A sensor interface is in communication with a physiological sensor. The physiological sensor is attached to a user to sense a physiological response to the dose. Physiological data is sent to the sensor interface. A controller is coupled to the sensor interface to collect the sensed physiological data from the user corresponding to the time that the aerated dose is delivered to the user. The effectiveness of the dose may be determined from the collected data. The dose amount or frequency may be changed or the drug may be changed based on the collected data.

18 Claims, 5 Drawing Sheets

(51) Int. Cl.
*A61B 5/0205* (2006.01)
*A61B 5/08* (2006.01)
*G16H 20/13* (2018.01)

(52) U.S. Cl.
CPC .......... *A61B 5/4833* (2013.01); *A61B 5/4848* (2013.01); *A61B 5/6801* (2013.01); *A61M 15/009* (2013.01); *G16H 20/13* (2018.01)

(58) Field of Classification Search
CPC ........ A61M 15/003; A61M 2016/0021; A61M 2205/3306; A61M 2205/332; A61M 2205/3368; A61M 2205/3375; A61M 2205/505; A61M 2230/005; A61M 2230/06; A61M 2230/205; A61M 2230/432; A61M 2230/50; A61M 2230/63; A61M 15/008; A61M 2205/3331; A61M 2205/3553; A61M 2205/3584; A61M 2205/52; A61M 2230/42; A61M 2230/43; A61B 5/0205; A61B 5/082; A61B 5/4833; A61B 5/4848; A61B 5/6801; A61B 5/4836; A61B 5/682; A61B 5/01; A61B 5/02416; A61B 5/02438; A61B 5/0836; A61B 5/11; A61B 5/6804; A61B 5/6823; A61B 5/6831; A61B 5/6832; A61B 5/6846
USPC ..................................................... 128/203.15
See application file for complete search history.

(56) References Cited

U.S. PATENT DOCUMENTS

2004/0031484 A1* 2/2004 Halamish .............. A61M 16/06 128/200.14
2005/0251289 A1* 11/2005 Bonney ................... A61P 11/08 705/3
2007/0023034 A1* 2/2007 Jongejan ............. A61M 15/009 128/200.14
2007/0163583 A1* 7/2007 Brand ............... A61M 15/0068 128/203.23
2009/0151718 A1* 6/2009 Hunter ................... A61B 5/087 600/538
2009/0314292 A1 12/2009 Overfield et al.
2010/0218759 A1* 9/2010 Anderson ......... A61M 15/0081 128/200.23
2016/0106935 A1 4/2016 Sezan et al.
2016/0144141 A1* 5/2016 Biswas ............... A61M 15/009 128/200.23
2016/0242675 A1* 8/2016 Perez De Alejo Fortun ............... A61B 5/087
2016/0325057 A1 11/2016 Morrison et al.
2016/0361013 A1* 12/2016 Schmid ................ A61B 5/0022
2017/0127727 A1 5/2017 Davidson et al.
2017/0332701 A1 11/2017 Fornarelli
2018/0140786 A1 5/2018 Calderon Oliveras et al.
2018/0204636 A1* 7/2018 Edwards ................ G16H 40/67
2018/0374561 A1* 12/2018 Binier .................... G16H 10/60
2019/0053540 A1 2/2019 Baker et al.
2019/0125990 A1* 5/2019 Holtz ................ A61M 15/0083
2020/0163389 A1* 5/2020 Sur ......................... A24F 40/50
2020/0195695 A1* 6/2020 Dagdeviren .......... H04L 67/125

FOREIGN PATENT DOCUMENTS

| | | | |
|---|---|---|---|
| CN | 104918651 | A | 9/2015 |
| CN | 105307717 | A | 2/2016 |
| EP | 1978460 | A1 | 10/2008 |
| JP | 2013523395 | A | 6/2013 |
| JP | 2018531055 | A | 10/2018 |
| WO | 2014/143842 | A1 | 9/2014 |
| WO | 2018/057058 | A1 | 3/2018 |

OTHER PUBLICATIONS

Written Opinion in International Patent Application No. PCT/IB2020/056099 mailed Aug. 14, 2020 (7 pp.).

* cited by examiner 100
150
152
114
120
112
110
122

100
114
152
150
120
132
112
130
140
110
134

114
210
224
220
226
212
230
SENSOR
SENSOR INTERFACE
CPU
TRANSCEIVER
RULES ENGINE
DOSE SENSOR
DOSING MECHANISM
100
228
222
240

FIG. 3A

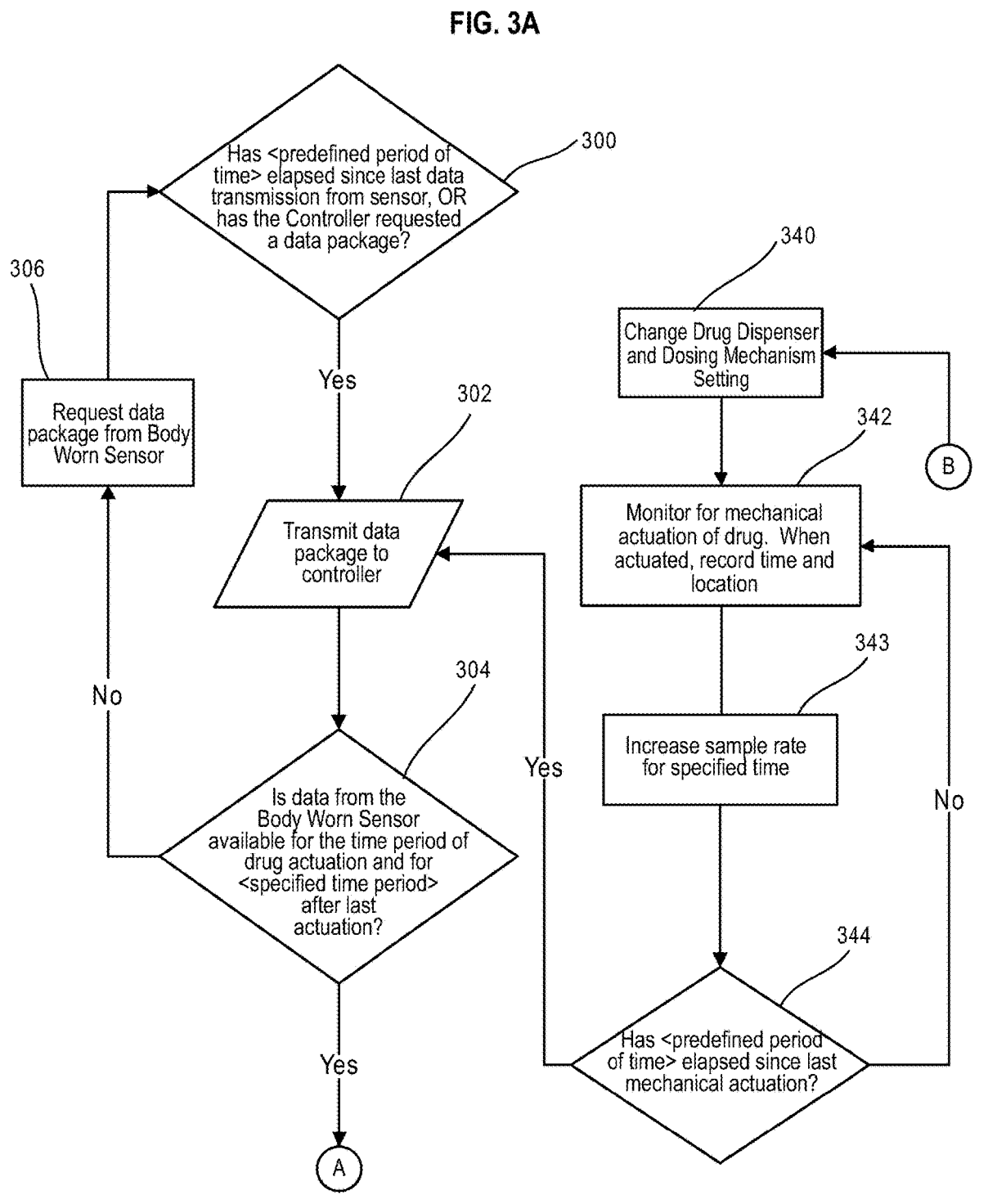

300
Has <predefined period of time> elapsed since last data transmission from sensor, OR has the Controller requested a data package?

Yes

302
Transmit data package to controller

304
Is data from the Body Worn Sensor available for the time period of drug actuation and for <specified time period> after last actuation?

Yes

A

No

306
Request data package from Body Worn Sensor

340
Change Drug Dispenser and Dosing Mechanism Setting

B

342
Monitor for mechanical actuation of drug. When actuated, record time and location 343
Increase sample rate for specified time 344
Has <predefined period of time> elapsed since last mechanical actuation?

Yes

No

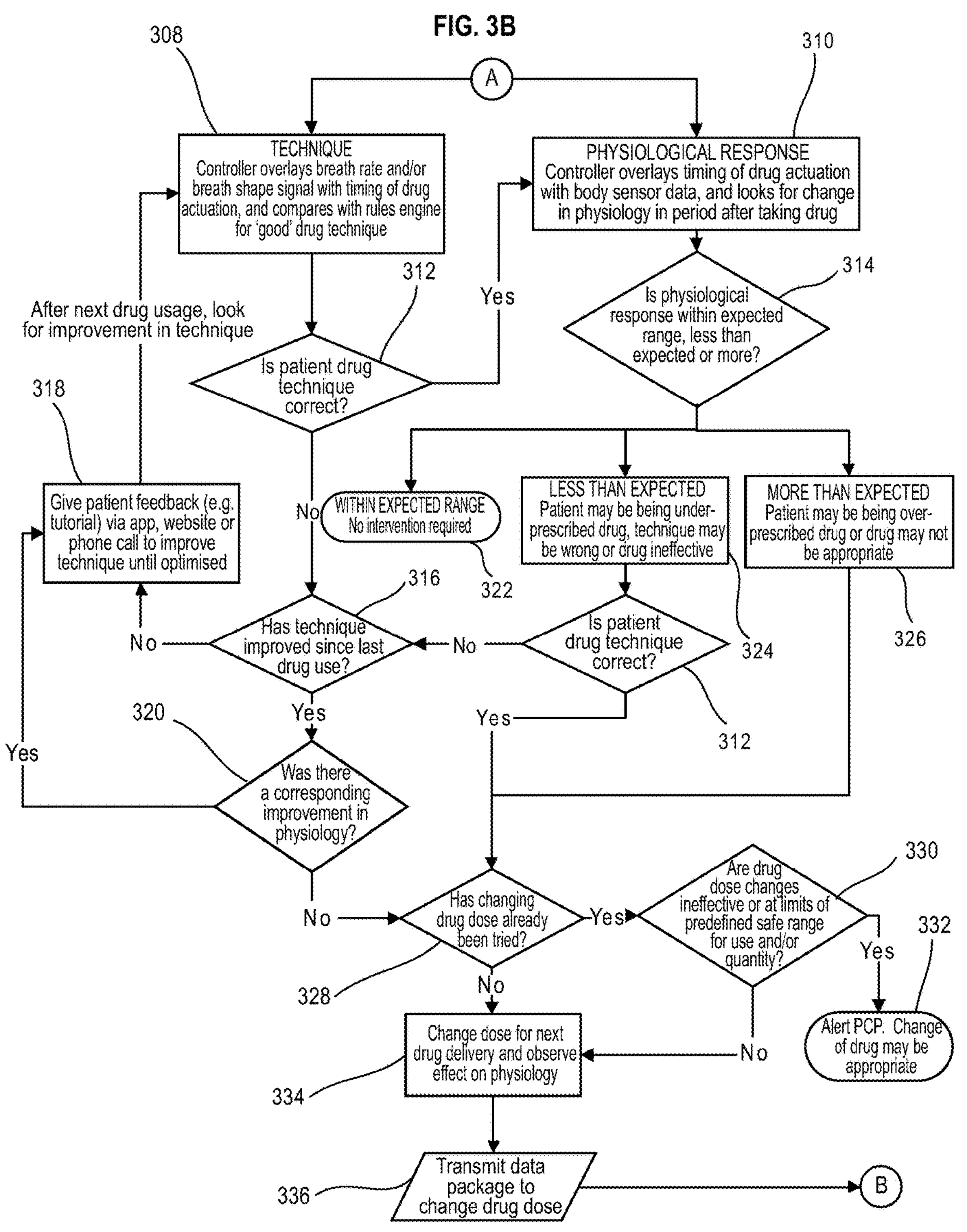
FIG. 3B
308
310
A
TECHNIQUE
Controller overlays breath rate and/or breath shape signal with timing of drug actuation, and compares with rules engine for 'good' drug technique
PHYSIOLOGICAL RESPONSE
Controller overlays timing of drug actuation with body sensor data, and looks for change in physiology in period after taking drug
312
Yes
314
After next drug usage, look for improvement in technique
Is patient drug technique correct?
Is physiological response within expected range, less than expected or more?
318
Give patient feedback (e.g. tutorial) via app, website or phone call to improve technique until optimised
No
WITHIN EXPECTED RANGE
No intervention required
LESS THAN EXPECTED
Patient may be being under-prescribed drug, technique may be wrong or drug ineffective
MORE THAN EXPECTED
Patient may be being over-prescribed drug or drug may not be appropriate
322
316
No
Has technique improved since last drug use?
No
Is patient drug technique correct?
324
326
Yes
Yes
312
320
Yes
Was there a corresponding improvement in physiology?
330
No
Has changing drug dose already been tried?
Yes
Are drug dose changes ineffective or at limits of predefined safe range for use and/or quantity?
Yes
332
328
No
Change dose for next drug delivery and observe effect on physiology
No
Alert PCP. Change of drug may be appropriate
334
336
Transmit data package to change drug dose
B

SYSTEM AND METHOD FOR CONTROLLING INHALER DOSAGE

PRIORITY CLAIM

This application claims the benefit of and priority to PCT Application No. PCT/IB2020/056099, filed Dec. 27, 2020, which claims the benefit of and priority to U.S. Provisional Application No. 62/868,300, filed Jun. 28, 2019, which are both is hereby incorporated by reference herein in their entirety.

TECHNICAL FIELD

The present disclosure relates generally to inhalers, and more specifically for an inhaler system that adjusts dosage according to effectiveness of the dose.

BACKGROUND

Currently, many patients with ailments are provided an inhaler to provide dosages of drugs. For example, an asthma patient may be provided a stimulant to assist mucus and reducing inflammation in clearing up breathing passages. Thus, when the patient experiences asthma exacerbations, the patient can put the inhaler in front their mouth and activate the inhaler spray, delivering a dose of the drug into the lungs in order to relieve the symptom.

A known inhaler for inhalation of drugs has a housing at least partially defining a flow passageway extending through the inhaler from an air inlet to an outlet. A pressurized metered dose canister is contained in the housing. The canister includes a valve stem and a metering valve arranged to seat in a valve stem block formed on the housing and a main canister body of the canister may be moved relative to the housing and valve stem so as to operate the metering valve and fire a metered dose of propellant and active drug through the valve stem block and into the flow passageway. By depressing the canister, when a user sucks on a mouthpiece of the housing, air may be drawn into the housing between the canister and an inner wall of the housing and may flow along past the canister towards the outlet. This type of inhaler often works well, but some users may find it difficult to coordinate an inward breath for inhalation with firing of the canister and, if the canister is fired too early or late relative to an inhalation breath, optimum inhalation may not be achieved.

Another type of inhaler is a dry powder inhaler that dispenses medicament from a single use capsule. In such an inhaler, a user loads the capsule in the inhaler. The inhaler has a mouthpiece that a user may place in their mouth. A user then activates a mechanical push button that perforates the capsule. The medicament is released from the pierced capsule when air is drawn through air passages and swirled within the inhaler. The user then inhales the drug. However, this type of inhaler also suffers from inability of users to coordinate their breath, thus preventing optimal inhalation. If the user's inhalation is too weak, the device may not be able to aerosolize a full dose of medication. Thus, the ability of a breath-actuated inhaler to deliver a proper dose of medication may be compromised if the user has limited lung capacity and/or lung function.

Jet nebulizers may enable users to receive medication using their normal breathing patterns and, thus, may deliver medication without requiring any forceful inhalations. However, jet nebulizers are often inefficient. The devices may nebulize more medication than can be inhaled during a single inspiratory effort. As such, significant portions of the nebulized medication may be lost during the expiratory cycle of a user's breathing pattern.

Thus, current inhalers are inefficient in their delivery of the drug. If the patient's technique is poor much of the aerated drug ends up on the inside of patient's mouths and thus a large portion of the drug is not delivered. Similarly, if the drug is released at the incorrect moment in the inhalation-exhalation cycle the drug will not reach the part of the lung where it is needed to act.

Current inhalers also do not allow the adjustment of inhaler dosage. Thus dosages are fixed and cannot be finely tuned to factors such as patient physiology (size, weight, gender, etc.), type of lung disorder, and stage of disease progression. Current inhalers also do not have any feedback on drug effectiveness and thus it is not possible to measure the effectiveness of inhaler dosage, or whether the drug is having the desired physiological effect, or even whether a patient is properly using the inhaler. Certain advanced inhalers may provide some electronic indicators that the pump has been activated and thus may report when an inhaler has been activated to interested parties such as physicians or payors.

Thus, the most advanced current inhaler systems allow physicians and/or payors only to determine that the pump on an inhaled drug has been activated. A deduction that proper use of the inhaler by a patient may be made. However, such systems do not allow any means for determining whether the drug has had any effectiveness. Thus, the drug may have been delivered into the air, or the canister may be empty, or the patient's technique may have been so poor no drug reached the desired section of the lungs. This prevents immediate remote intervention in the patient's health in real-time. Currently, an intervention cannot occur until the patient visits their physician (which may be months later), or when they present a health exacerbation to a hospital because the drug has been ineffective. This can create more long-term damage to the patient's condition and is costly to health systems.

There is a need for an inhaler that collects data on dosage effectiveness based on sensed physiological parameters from the patient. There is also a need for an inhaler that allows adjustment of dosage based on the effectiveness of the drug. There is a further need for an inhaler that allows feedback as to whether a patient is properly using the inhaler.

SUMMARY

One disclosed example is an inhaler including an actuator to hold a drug container. The inhaler includes a dosing mechanism operable to aerate a dose from the drug container. The dosing mechanism provides the aerated dose to a user. A sensor interface is in communication with a physiological sensor. The physiological sensor is attached to a user to sense a physiological response to the dose and send physiological data to the sensor interface. A controller is coupled to the sensor interface to collect the sensed physiological data from the user corresponding to the time that the aerated dose is delivered to the user.

A further implementation of the example inhaler is an embodiment where the controller is operable to determine the effectiveness of the dose based on the physiological data. Another implementation is where the controller is operable to change the volume of the aerated dose via the dosing mechanism in response to the effectiveness of the dose. Another implementation is where the inhaler includes a pressure sensor. The controller determines the occurrence of an inhalation point of the user from the output of the pressure sensor relative to the provision of the aerated dose. Another implementation is where the controller is operable to control the dosing mechanism to provide the aerated dose to the user at the inhalation point. Another implementation is where the physiological sensor is an oxygen sensor. The controller is operable to detect the oxygenation in the user based on the output of the sensor, and determine the effectiveness of the dose based on the level of oxygenation in the user. Another implementation is where the physiological sensor is a heart rate sensor. The controller is operable to detect the heart rate in the user based on the output of the sensor, and determine the effectiveness of the dose based on the heart rate of the user. Another implementation is where the physiological sensor is a carbon dioxide sensor. The controller is operable to detect the breathing in the user based on the output of the sensor, and operable to determine the effectiveness of the dose based on the carbon dioxide of the breath of the user. Another implementation is where the controller is operable to determine data associated with the breath of the user. The controller is operable to analyze the effectiveness of the dose based on the data associated with the breath of the user. Another implementation is where the controller is operable to determine the effectiveness of the technique applied by the user in activating the inhaler by comparing a breath shape derived from the data and a rule indicating dosage technique. Another implementation is where a mobile computing device associated with the user receives a communication to improve technique based on the effectiveness of the technique. Another implementation is where the inhaler includes a transceiver to transmit the collected data to an external device. The transceiver receives control data for regulating the pump to change the volume of the aerated dose provided by the pump in response to analysis of the collected data. Another implementation is where the external device is a mobile computing device associated with the user. The external device executes an application to analyze the collected data to determine the control data. Another implementation is where the physiological sensor is operative to increase a sample rate when the dosing mechanism provides the drug dose. Another implementation is where the dosing mechanism is a pump. Another implementation is where the drug container is one of a single dose capsule or a multiple dose canister.

Another disclosed example is an inhaler based data collection system. The system includes a physiological sensor coupled to a user and an inhaler mateable with a drug container. The inhaler includes a dosing mechanism operable to aerate a dose from the drug container. The dosing mechanism provides the aerated dose to the user. A sensor interface is coupled to the physiological sensor to sense a response to the dose. The inhaler includes a controller to collect physiological data from the user corresponding to the time that the aerated dose is delivered to the user and a transceiver. A data server receives the collected physiological data from the transceiver. An analysis module is operable to determine the effectiveness of the dose based on the collected physiological data.

A further implementation of the example data collection system is an embodiment where the analysis module is operable to send control data to the transceiver changing the amount of the aerated dose from the pump in response to the effectiveness of the dose. Another implementation is where the analysis module is operable to determine a change in the frequency to aerate a dose in response to the effectiveness of the dose. Another implementation is where the controller is operable to determine the occurrence of an inhalation point of the user from the output of the sensor, and the controller correlates the timing of the provision of the aerated dose to the inhalation point. Another implementation is where the analysis module is operable to determine the effectiveness of the technique applied by the user in activating the inhaler by comparing the inhalation point and a rule indicating inhaler technique. Another implementation is where the analysis module is operative to send a communication to the user to improve inhaler technique based on the effectiveness of the inhaler technique. Another implementation is where the physiological sensor is an oxygen sensor, and where the analysis module is operable to detect the oxygenation in the user based on the output of the sensor. Another implementation is where the physiological sensor is a heart rate sensor, and where the analysis module is operable to detect the heart rate of the user based on the output of the sensor. Another implementation is where the physiological sensor is a carbon dioxide sensor, and where the analysis module is operable to detect the breathing in the user based on the output of the sensor. Another implementation is where the analysis module is operable to determine data associated with the breath of the user, and where the analysis module is operable to analyze the effectiveness of the dose based on the data associated with the breath of the user.

Another disclosed example is a dosage control unit for installation on an inhaler. The inhaler has an actuator holding a drug container containing a drug, and a dosing mechanism coupled to the drug container to aerate a dose from the drug container. The dosing mechanism provides the aerated dose to a user. The dosage control unit includes an interface attaching the controller unit to the inhaler. A dosing sensor detects the dosing mechanism aerating the dose. A sensor interface is in communication with a physiological sensor attached to the user of the inhaler. A controller is coupled to the dosing sensor and the sensor interface. The controller is operable to collect physiological data from the user corresponding to the time that the aerated dose is delivered to the user. The time is determined from the dosing sensor.

A further implementation of the example dosage control unit is an embodiment where the controller is operable to determine the effectiveness of the dose based on the sensor output. Another implementation is where the controller is operable to change the volume of the aerated dose via controlling the dosing mechanism in response to the effectiveness of the dose. Another implementation is where the dosage control unit includes a pressure sensor, where the controller is operable to determine the occurrence of an inhalation point of the user from the output of the pressure sensor relative to the provision of the aerated dose, and the controller further controls the dosing mechanism to provide the aerated dose to the user at the inhalation point. Another implementation is where the physiological sensor is an oxygen sensor, and where the controller is operable to detect the oxygenation in the user based on the output of the sensor, and is operable to determine the effectiveness of the dose based on the level of oxygenation in the user. Another implementation is where the physiological sensor is a heart rate sensor, and where the controller is operable to detect the heart rate in the user based on the output of the sensor, and is operable to determine the effectiveness of the dose based on the heart rate of the user. Another implementation is where the physiological sensor is a carbon dioxide sensor, and where the controller is operable to detect the breathing in the user based on the output of the sensor, and operable to determine the effectiveness of the dose based on the carbon dioxide in the breath of the user. Another implementation is where the controller is operable to determine data associated with the breath of the user, the controller is operable to analyze the effectiveness of the dose based on the data associated with the breath of the user. Another implementation is where the controller is operable to determine the effectiveness of the technique applied by the user in activating the inhaler by comparing a breath shape derived from the data and a rule indicating inhaler technique. Another implementation is where the dosage control unit includes a transceiver to transmit the collected data to an external device, and to receive control data for the controller regulating the pump to change the volume of the aerated dose provided by the pump in response to analysis of the collected data. Another implementation is where the external device is a mobile computing device associated with the user, and where the external device executes an application to analyze the collected data to determine the control data. Another implementation is where the external device is a data server, and where the external device executes an application to analyze the collected data to determine the control data.

Another disclosed example is a method to measure the effect of a dose of a drug emitted by an inhaler. The inhaler has an actuator holding a drug container containing the drug and a dosing mechanism coupled to the drug container to aerate a dose from the drug container. The dosing mechanism provides the aerated dose to a user. A time that the dosing mechanism provides the aerated dose to the user is determined via a controller coupled to a dosing sensor. Physiological data of the user is measured via a physiological sensor attached to the user. The physiological data is collected and correlated with the aerated dose. The effectiveness of the dose is determined based on the collected physiological data.

A further implementation of the example method is an embodiment where the physiological sensor is an oxygen sensor, and wherein the determination of the effectiveness is based on the level of oxygenation in the user. Another implementation is where the physiological sensor is a heart rate sensor, and where the determination of the effectiveness is based on to the heart rate of the user. Another implementation is where the physiological sensor is a carbon dioxide sensor, and where the determination of the effectiveness is based on in response to the carbon dioxide of the breath of the user. Another implementation is where the determination of the effectiveness is performed by the controller. Another implementation is where the determination of the effectiveness is performed by an external device from the inhaler. Another implementation is a computer program product comprising instructions which, when executed by a computer, cause the computer to carry out the above-described method. Another implementation is where the computer program product is a non-transitory computer readable medium.

Another disclosed example is a method of regulate the technique of a user using an inhaler. The inhaler has an actuator holding a drug container containing the drug and a dosing mechanism coupled to the drug container to aerate a dose from the drug container. The dosing mechanism provides the aerated dose to the user. A time that the dosing mechanism provides the aerated dose to the user is determined via a controller coupled to a dosing sensor. Breath data of the user is measured via a sensor associated with the user. The breath data is collected and correlated with the time the dosing mechanism provides the aerated dose. An evaluation of the effectiveness of the user using the inhaler is provided based on the correlated breath data and the time the dosing mechanism provides the aerated dose.

A further implementation of the example method is an embodiment where the sensor is a pressure sensor, and where the breath data is associated with the output of the pressure sensor. Another implementation is where the sensor is a carbon dioxide sensor, and where the breath data is associated with the detected carbon dioxide of the user. Another implementation is where the determination of the effectiveness is performed by the controller. Another implementation is where the determination of the effectiveness is performed by an external device from the inhaler. Another implementation is a computer program product comprising instructions which, when executed by a computer, cause the computer to carry out the above-described method. Another implementation is where the computer program product is a non-transitory computer readable medium.

Another disclosed method is a method to monitor the effectiveness of a drug applied by an inhaler. The inhaler has an actuator holding a drug canister containing the drug and a dosing mechanism coupled to the drug canister to aerate a dose from the drug canister. The dosing mechanism provides the aerated dose to a user. A time that the dosing mechanism provides the aerated dose to the user is determined via a controller. Physiological data of the user is measured via a physiological sensor associated with the user. The physiological data is collected and correlated the aerated dose. The effectiveness of the dose is determined based on the collected physiological data.

Another implementation is a computer program product comprising instructions which, when executed by a computer, cause the computer to carry out the above-described method. Another implementation is where the computer program product is a non-transitory computer readable medium.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims.

BRIEF DESCRIPTION OF THE DRAWINGS

The disclosure will be better understood from the following description of exemplary embodiments together with reference to the accompanying drawings, in which:

FIG. 3 is a flow diagram of an algorithm to process the data from the inhaler in FIG. 1A and provide dosage control and technique analysis;

Figures 1A, 1B, 2:
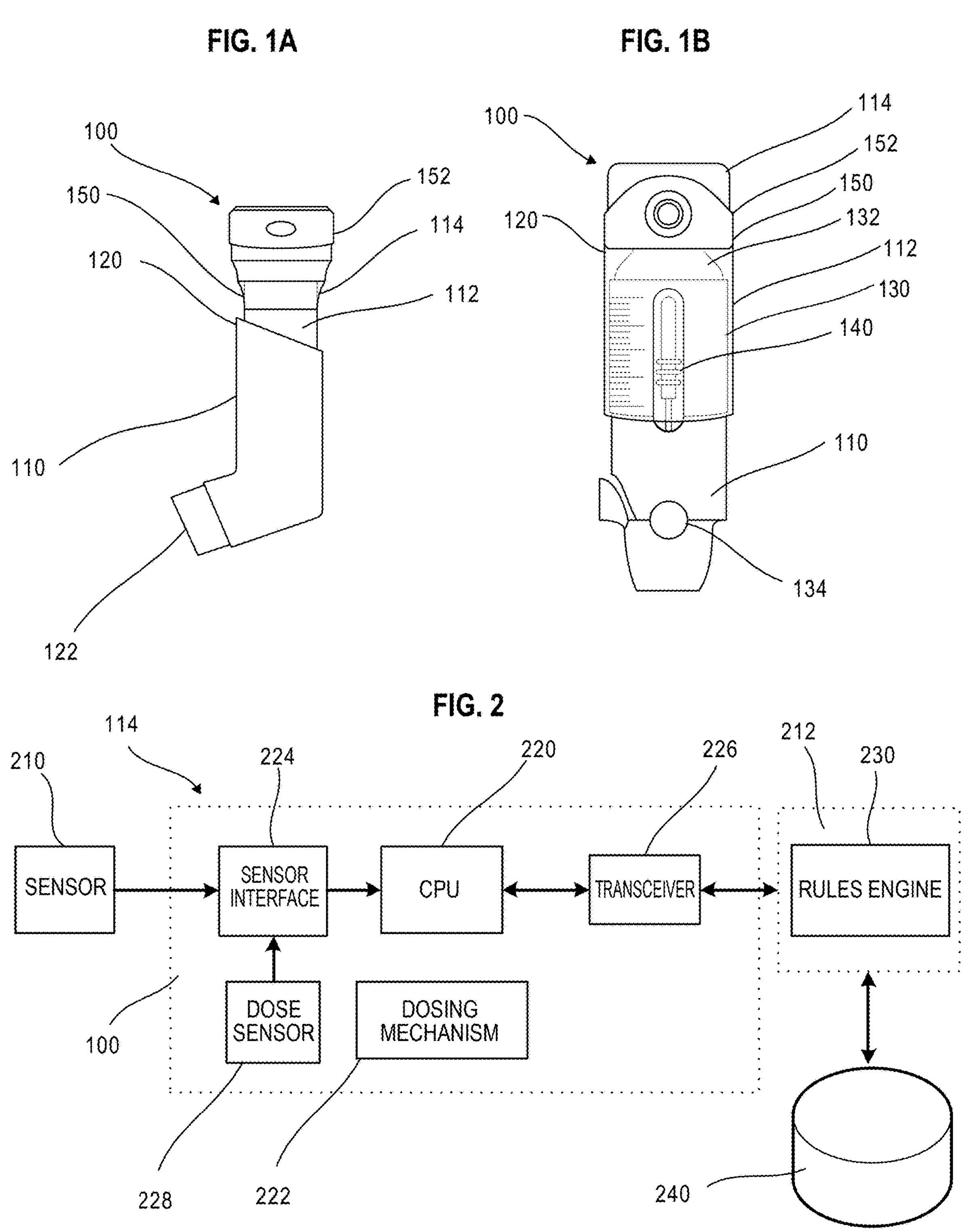
FIG. 1A is a side view of an example inhaler based system incorporating a physiological sensor to evaluate the effectiveness of a drug dose.
FIG. 1B is a front view of the inhaler in FIG. 1A.
FIG. 2 is a block diagram of the controller of the inhaler and sensor in FIG. 1A.

The present disclosure is susceptible to various modifications and alternative forms. Some representative embodiments have been shown by way of example in the drawings and will be described in detail herein. It should be understood, however, that the invention is not intended to be limited to the particular forms disclosed. Rather, the disclosure is to cover all modifications, equivalents, and alternatives falling within the spirit and scope of the invention as defined by the appended claims.

DETAILED DESCRIPTION OF THE ILLUSTRATED EMBODIMENTS

The present inventions can be embodied in many different forms. Representative embodiments are shown in the drawings, and will herein be described in detail. The present disclosure is an example or illustration of the principles of the present disclosure, and is not intended to limit the broad aspects of the disclosure to the embodiments illustrated. To that extent, elements and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at," "near," or "nearly at," or "within 3-5% of," or "within acceptable manufacturing tolerances," or any logical combination thereof, for example.

The present disclosure relates to a smart inhaler system that allows efficient dosages to be applied according to individual user feedback. An aerosol drug delivery system is combined with a body-worn sensor that measures the patient's physiological response to that drug. The drug delivery system tracks time, frequency and dosing of the drug, while the body-worn sensor tracks one or some combination of i) blood oxygenation, ii) heart rate, iii) carbon dioxide levels in the blood, iv) breath rate, v) breath shape or vi) gas composition of the breath. Both transmit this data to a control system where it is analysed and control data may be provided back to the delivery system to more efficiently administer drug doses. The data may also be analyzed to provide diagnostic information regarding the effectiveness of the drug and the proper operation of the inhaler by the user.

Examples of inhalers and drugs that may incorporate the principles detailed below include SABA relievers that include a Bricanyl Turbuhaler administering terbutaline, and a Ventolin Inhaler, Aiomir Autohaler or an Asmol Inhaler administering salbutamol. Examples for non-steroidal preventers include an Intal inhaler administering sodium cromoglycate and a Tilade inhaler administering nedocromil sodium. Examples for ICS preventers include a Flixotide inhaler, a Flixotide Accuhaler, and a Fluticasone Cipla inhaler administering fluticasone propionate, a QVAR inhaler or a QVAR autohaler administering beclometasone, or a a Pulmicort Turbuhaler administering budesonide. An example for SAMA medication is an Atrovent Metered Aerosol administering ipratropium. Examples of ICS/LABA combinations include a Symbicort Turbuhaler, a Symbicort Rapihaler, or a DuoResp Spiromax administering budesonide/formoterol, a Seretide MDI, a Seretide Accuhaler or a Fluticasone+Salmeterol Cipla Inhaler administering fluticasone propionate/salmetero, a Flutiform Inhaler administering fluticasone propionate/formotero and a Breo Ellipta administering fluticasone furoate/vilanterol. Examples of LABA medications include an Oxis Turbuhaler administering formoterol, a Serevent Accuhaler administering salmeterol, and an Onbrez Breezhaler administering indacaterol. Examples of LAMA medication includes a Spiriva Respimat and a Spiriva Handihaler administering tiotropium, a Bretaris Genuair administering aclidinium, an Incruse Ellipta administering umeclidinium, and a Seebri Breezhaler administering glycopyrronium. An example of ICS/LAMA/LABA is a Trelegy Ellipta administering fluticasone furoate/umeclidinium/vilanterol. Examples of LAMA/LABA combinations include a Spiolto Respimat administering tiotropium/olodaterol, an Ultibro Breezhaler administering indacaterol/glycopyrronium, a Brimica Genuair administering aclidinium/formoterol, and an Anoro Ellipta administering umeclidinium/vilanterol.

FIG. 1A is a side view of an example smart inhaler 100. FIG. 1B is a front view of the example smart inhaler 100. The inhaler 100 includes a semi-cylindrical actuator 110, a dosage container such as a canister 112, and a spray controller assembly 114. The spray controller assembly 114 includes a controller and other electronics to regulate the dose from the canister 112 and collect physiological measurement data from an external sensor. The actuator 110 includes an open end 120 and a mouthpiece 122. The actuator 110 allows the canister 112 to be loaded to the open end 120. Typically, a cap (not shown) may be inserted over the mouthpiece 122 to protect the interior of the actuator 110 from contaminants when not in use.

The canister 112 includes an enclosure 130 that includes a closed end 132 and an actuator nozzle 134 on the opposite end. The enclosure 130 holds a gas phase and a liquid phase that is the drug. A dosing mechanism such as a pump 140 having a metering valve is installed in the middle of the enclosure 130. The canister 112 includes a metering chamber that is connected to an expansion chamber. When pressure is applied by the user to the closed end 132 through pressing the spray controller assembly 114 to compress the canister 112, the enclosure 130 moves relative to the metering valve causing pressure on the pump 140 to aerate a dose and provide the dose to the user from the actuator nozzle 134.

In this example, the controller assembly 114 includes a mating collar 150 that is part of a cylindrical container 152. The mating collar 150 mates with the open end of the actuator 110 and allows contact with the closed end 132 of the enclosure 130. The user may thus apply pressure to the top of the cylindrical container 152 to actuate the pump 140 in the canister 112. Thus, existing inhalers that only include the actuator 110 and the canister 112 may be mated with the controller assembly 114 to collect the data and control the volume of the drug dose by controlling the pump 140 as will be described below. The controller assembly 114 includes electronics that collect data on the usage of the inhaler 100 based on inputs from a sensor and timing data when a dose is administered by compressing the canister 112. It is to be understood that other types of aerosol inhalers may integrate the components of the controller assembly 114 in the inhaler.

As explained above, the principles explained in this disclosure may be applied to other types of inhalers such as a dry powder inhaler that uses drug containers in the form of single dose capsules. The dosing mechanism in the dry powder inhaler is a mechanical push button that when activated perforates the capsule. The medicament is released from the pierced capsule when air is drawn through air passages and swirled within the inhaler. The user then inhales the drug. A similar controller assembly may either be integral with the inhaler or be a module that may be mated with existing "dumb" dry powder inhalers to allow the collection of data to determine effectiveness of the drug doses.

FIG. 2 is a block diagram of the components of the controller assembly 114 in an inhaler data collection system 200. The system 200 includes the inhaler 100 and controller assembly 114, a physiological sensor 210 mounted on a user, and a remote external device 212. The inhaler 100 includes a controller 220, a drug dispenser and dosing mechanism 222, a sensor interface 224, and a transceiver 226. The controller 220 may include an internal memory or a memory device may be included in the controller assembly 114. Such a memory may be a volatile type computer memory, including for example RAM, DRAM, SRAM, may be used. In such instances, the adherence monitor may continually transmit information to the computing device external to the adherence monitor or medicament delivery device. In other embodiments non-volatile memory formats may be used, including for example ROM, EEPROM, flash memory, ferroelectric RAM (F-RAM), optical and magnetic computer memory storage devices, and others. The memory may be used to store data collected by the control assembly 114.

The sensor interface 224 is in communication with the sensor 210 to receive data from the sensor 210. In this example, the communication may be via a cable or a wire. Alternatively, a wireless communication may be established between the sensor interface 224 and the sensor 210. The transceiver 226 allows exchange of data between the inhaler 100 and control data from the remote external device 212 via a wireless or a wired connection. The inhaler 100 also includes a dosage sensor 228 that records when a dose is administered by a user activating the inhaler 100. In this example, the wireless communication may be any suitable protocol including Bluetooth Low Energy. Wi-Fi (IEEE 802.11), Bluetooth®, other radio frequencies, Infra-Red (IR), GSM, CDMA, GPRS, 3G, 4G, W-CDMA, EDGE or DCDMA200 or similar protocols.

In this example, the dosing mechanism 222 may include a spring control that regulates the force applied to the canister 112 and therefore the dosage applied from the canister. Alternatively, the dosing mechanism 222 may be controlled to be activated at a predetermined time by the controller 220 in response to an activation motion by the user.

In this example, the body worn sensor 210 may be a photoplethysmograph that regularly records a patient's physiological data such as oxygen saturation correlated to the effect of the drug against a time stamp. In this example, the time stamp is provided by the remote external device 212 through the controller assembly 114. Alternatively, the controller 220 on board the controller assembly 114 may provide the timestamp. In one example, both the external sensor 210 and the air pressure sensor 228 may both receive a timestamp from the external device 212 independently. In another example, the inhaler sensor 228 acts as a master and the body-mounted sensor 210 acts as a slave device receiving the time stamp from the inhaler sensor 228. The time stamp may also be provided by a clock device in the sensor 210. Such data may include baseline heart rate, breath rate, breath shape, oxygen saturation, CO2 saturation or breath gas composition.

As will be explained below, the data from the sensor 210 is used to determine the effectiveness of the dose administered from the inhaler 100. Thus, in this example, the data is provided in a data package by the sensor 210 that includes a predetermined number of sensor measurements over a period of time. For example, a standard or baseline sampling rate could be monitoring heart rate for 15 seconds every 60 seconds, or oxygen saturation for 30 seconds every 5 minutes. A data package could be a record of the number of heart beats for 15 seconds every minute, over 24 hours. Alternatively, a collection of blood oxygen saturation waveforms taken every 5 minutes over 24 hours. The body worn sensor 210 may be in communication with the controller 220 via the sensor interface 224. On detection of an administration of a drug dose, the controller 220 can increase the sampling rate of the sensor 210 for a specified period of time, such as for 30 minutes, to obtain more data to evaluate the effectiveness of the dose. After the specified period of time, the sampling rate returns to the baseline sample rate to conserve the power for the sensor 210. The body-worn sensor 210 can receive a control signal to increase the sampling rate either directly from the external device 212 or directly from the controller 220 on the controller assembly 114. Use of the controller 220 allows data sampling even if the external device 212 is not powered or disconnected.

In this example, the body worn sensor 210 may be part of a device such as a wrist mounted health monitor, a diaphragm-mounted respiratory monitor worn inside underwear, a chest-mounted acoustic monitor attached to the skin or sewn into a shirt, a permanent health monitor inserted underneath the skin, or a mobile computing device. The sensor 210 may also include doppler radar motion sensors, accelerometers, thermometers, or scales, each of which is configured to provide additional physiological data (biomotion, physical activity, temperature, and weight, and oxygen saturation respectively) measured from the user. Optionally, the sensor 210 may be one of several sensors monitoring the user. As will be explained below, the data from the sensor 210 is used to determine the effectiveness of the dose administered from the inhaler 100.

In this example, the dosage sensor 228 is an air flow sensor may be mounted in the air path of the inhaler 100 to provide air pressure/flow data to determine the relationship between when the user started their inhalation and when they triggered the drug. There is a window of time after inhalation has begun that is optimal for effective drug delivery. If the user triggers before inhalation or too soon after the drug will not reach the desired part of the airway. The controller 220 may be operable to read the output of the air pressure sensor 228 and determine the optimal time during a breath cycle to activate the pump to release an aerated dose of the drug in response to the user applying pressure to the controller assembly 114. For example, the controller 220 may delay the activation of the pump until the data from the dose sensor 228 indicates the user is inhaling air. Other sensors may be configured to detect that the dose of the medicament is dispensed. The dose detection means may include one or more of an acoustic sensor, vibrational sensor, thermistor, pressure sensor, pressure switch, force sensor resistor, audible sensor, optical sensor or proximity sensor, or mechanical switch. Depending on the type of switch or sensor selected, different signals may be used to detect a dose detection being dispensed such as a change in pressure, temperature, volume, visible or IR light intensity, etc. may be used to determine whether a dose has been delivered. Further, a combination of two or more sensor readings may be used to further determine whether a dose has been delivered.

The remote external device 212 may be a portable computing device such as a smart phone that executes an application to determine control data for the controller 220 to control the pump 140 in FIG. 1B to increase or decrease the volume of the dose provided by the inhaler 100. Alternatively, the remote device 212 may be an application server that includes a rules engine 230. The remote external device 212 may include access to a database 240 that includes big data from other inhaler users. Such data may be used to refine the baseline comparison to determine whether a drug is having the desired effect. The database 240 may also include other relevant data relating to the user of the inhaler to assist in evaluation of whether the user is employing the inhaler 100 to apply the drug dose with a correct technique.

FIG. 3A-3B is a flow diagram of the operational routine executed by the controller 220 of the smart inhaler 100 and the application on the remote external device 212. The controller 220 first determines whether a predefined period of time has elapsed since the last data transmission from the sensor 210 (300). In this example, the predefined period of time may be 24 hours. Alternatively, the controller 220 may request transmission of a data packet from the sensor 210 on a periodic basis or when the controller 220 determines a dose has been applied by the inhaler 100. In this example, the data packet includes physiological data that indicates the breath rate of the user or patient in response to the drug dose. If a transmission period elapses or if requested by the controller 220, the body sensor 210 transmits a data package to the controller 220 (302). The routine then determines whether data from the body sensor 210 is available for the time period of drug actuation when the user uses the inhaler 100 to apply a dose of the drug (304). If data is not available, the routine will request a data package from the body sensor 210 (306). In this example, the controller 220 may trigger a request for a higher sampling rate by the body sensor 210 after drug dosing. The controller 220 will then automatically transmit that high-resolution data after a predefined period of time, such as 20-30 minutes, after the drug dose is administered.

If the data is available, the routine evaluates the data to determine whether “good” drug delivery technique is being exercised using the rules engine 230 (308). For example, the routine may overlay a breath rate and/or breath shape signal with the timing of the drug actuation from the inhaler 100, and compare the data with a good drug delivery technique template from the rules engine 230. Maximum effectiveness may be the activation of the inhaler 100 at a point when a user inhales a breath in a breath shape. The ideal breath shape and correlated activation of the drug delivery is compared with the actual activation time in the breath shape taken from the data collected from the inhaler. For example, the ideal activation occurs if a user triggers the drug dose about 0.25-1 seconds after they start inhaling. The actual start of the inhalation signal will be a sudden drop in pressure or an increase in flow in the inhaler that may be compared to the ideal. For example, if there is a 2 second lag the user may receive coaching to change their technique. The algorithm that defines if a post-drug physiological response is “right” or “wrong” is driven by two datasets in this example. Initially, lab-based testing of patients with an ailment that requires treatment by the drug will be used to determine the baseline physiological response. For example, in the case of a drug to treat COPD, lab-based testing of COPD patients is used to track how respiratory rate, heart rate, SPO2, breath shape and other relevant physiological parameters change with taking a range of drugs. This dataset will define statistical boundaries to changes in respiratory rate, heart rate, SPO2, breath shape and other relevant physiological parameters from the patient’s normal baseline. For example, lab testing may define “expected range” of response for an emphysemic patient taking a bronchodilator to be “14-26% reduction in heart rate from patient baseline within 5-12 minutes of inhalation.”

Once users begin to take the drugs, the first dataset is augmented by a real-world second dataset. This second set will reveal insights such as “patients who have xxx change in RR, HR, SPO2, etc., after they have taken their bronchodilator are 62% less likely to be hospitalized in the subsequent 12 months.” In this example, an objective may be to manage a pulmonary condition to keep patients healthy at home. Thus, the second dataset may lead to a more nuanced algorithm that defines the “right” and “wrong” physiological response.

The routine also determines a physiological response of the user to the drug dose by overlaying the timing of the drug actuation with the physiological data from the body sensor 210 and determines changes in user physiology in the time period after inhaling the drug dose. (310). The routine compares the timing of the drug dosing with the timing of the patient’s inhalation-exhalation, and also looks for changes in the patient’s physiology that indicate whether the drug has been effective. On the basis of this information the routine may be employed in intervention procedures to optimize the drug’s effectiveness by changing the user’s drug-inhalation behaviour or, in consultation with a qualified physician, to vary the drug dose, vary the frequency of the dosing, or recommend a change in drug type.

After the comparison with correct technique (308), the routine determines whether the drug inhalation technique is correct according to the rules engine 230 (312). If the drug inhalation technique is within the rule, the routine determines whether the physiological data from the user is within the expected range or either less than the expected range or greater than the expected range (310). If the determined drug inhalation technique is not correct according to the rules engine 230, the routine determines whether the technique has improved since the last significant use of the inhaler 100 based on the analysis of the rules engine 230 (316). If the drug inhalation technique has not improved, the routine will provide the user feedback through an application, messaging or other media to improve the technique (318). If the technique has improved, the routine determines whether there was a corresponding improvement in physiology based on the information gathered in step 310 (320).

After overlaying the timing of the drug actuation with data relating to changes in physiology, the routine determines whether the physiological response is within the expected range (314). For example, if the patient is using a bronchodilator, in the 5-10 minutes after drug inhalation there should be a deepening of the breath shape (deeper and longer inhalation and exhalations), a slowing of the breath rate and potentially also a slowing of the heart rate. If the physiological response is within the expected range (322), the routine ends as no intervention is necessary. If the physiological response is less than expected (324), this may be symptomatic of under-prescription of the drug, incorrect technique, or drug ineffectiveness. The routine then determines whether the patient drug technique is correct (312). If the physiological response is more than expected (326), this may be a result of over-prescription of the drug, or that the drug is not appropriate for the condition of the patient. Thus, if there was an improvement in physiology (320), the drug delivery technique was correct (312) or the physiological response is more than expected (326), the routine determines whether changing the drug dose has already been attempted with the patient (328).

If changing the drug dosage has already been attempted, the routine determines whether the changes were ineffective or at the limits of the predefined safe range for use or quality of the drug (330). If the changes are ineffective or at the limits (330), the prescriber of the drug such as a health care professional is altered that a change of the drug may be appropriate (332). If changing the dose has not been attempted (328) or the changes have been found effective or not at the limit of the drug (330), the routine recommends changing the dose for the next delivery and observing the effect on physiology (334). The routine then transmits a data package to the inhaler 100 to change the drug dose (336). The data package is received, and the controller 220 in FIG. 2 may change a drug dispensing and dosing mechanism setting to reflect the new dose amount (340). Alternatively, the patient may be given instructions by a health care professional or through a mobile device to increase the frequency of taking doses of the drug. The controller 220 then monitors for mechanical actuation of the inhaler 100 by the user and records the time and location of the actuation (342). The controller 220 increases the sampling rate of the body sensor 210 for a predetermined period to obtain data on the effectiveness of the new dose amount (343). The controller 220 determines whether a predefined period of time such as 24 hours has elapsed since the last actuation (344). If the time period has elapsed, the controller 220 causes a data package from the sensor 210 to be sent to the controller 220. If the predetermined period of time has not elapsed the routine loops back and monitors for mechanical actuation (342).

The above described system provides quantified evidence to actors such as the user or patient, a payor, or a health care professional that a particular drug is managing the health of a user or patient as intended. The data provided from the controller 220 in FIG. 2 may provide evidence that the desired physiological effect is occurring from application of the drug. As explained above, a mechanism to remotely intervene to optimize the drug dosing from the inhaler may be provided to the user or patient directly or by a health care provider, if the drug dosage from the inhaler is currently being under-used or over-used. The routine in FIG. 3A-3B gives visibility to whether the end goal of desired effect on the patient's physiology is achieved by the drug administered from the inhaler 100.

Current inhalers deliver the same dose per pump irrespective of disease type, patient size, gender, age, metabolic rate, short-term periodic health changes (e.g. exacerbations) and long-term health deterioration. The above analysis routine adjusts for these variations by analyzing physiological feedback to personalize the dose to the patient. Thus, the amount of the dose may be changed if the inhaler is capable of changing the dose, or the frequency of the dose may be changed via instructions to the user, or a different drug may be prescribed.

Figure 4:
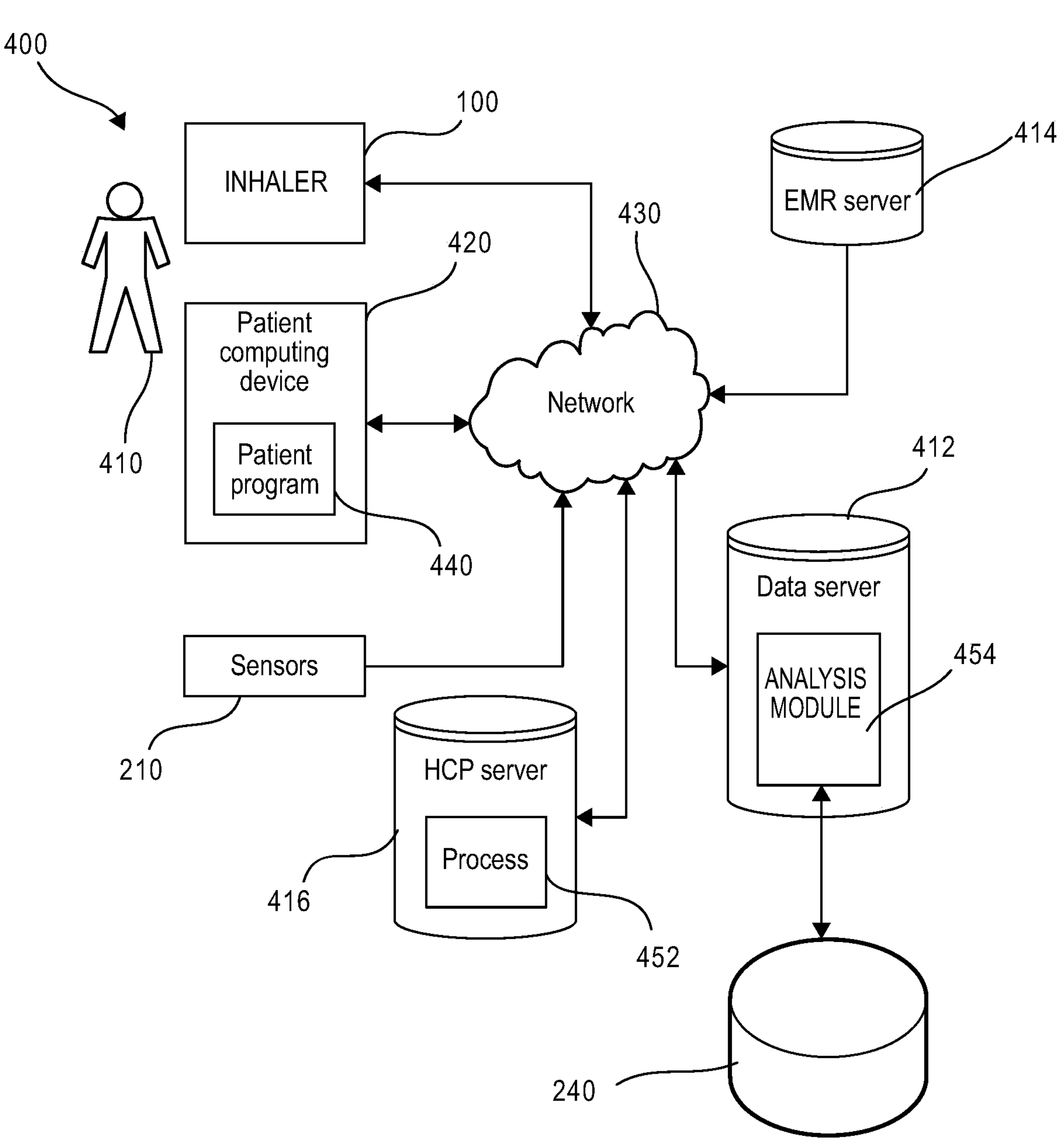
FIG. 4 is a block diagram of a health care system that supports the inhaler system in FIG. 1A.

FIG. 4 is a block diagram of an example health care system 400 for obtaining data from is a block diagram of an example health care system 400 for obtaining data from patients using inhalers such as the inhaler 100 in FIG. 1. The health care system 400 includes an inhaler such as the inhaler 100 in FIG. 1 that provides drug dosages to a user or patient 410. The health care system 400 includes a data server 412, a electronic medical records (EMR) server 414, a health or home care provider (HCP) server 416, a patient computing device 420, and one or more physiological sensors that may include the sensor 210 in FIG. 2. The patient computing device 420 and physiological sensors are co-located with the patient 410 and the inhaler 100 in this example. In the system 400, these entities are all connected to, and configured to communicate with each other over, a wide area network 430, such as the Internet. The connections to the wide area network 430 may be wired or wireless. The EMR server 414, the HCP server 416, and the data server 412 may all be implemented on distinct computing devices at separate locations, or any sub-combination of two or more of those entities may be co-implemented on the same computing device.

The patient computing device 420 may be a personal computer, mobile phone, tablet computer, or other device. The patient computing device 420 is configured to intermediate between the patient 410 and the remotely located entities of the system 400 over the wide area network 430. In the implementation of FIG. 4, this intermediation is accomplished by a software application program 440 that runs on the patient computing device 420. The patient program 440 may be a dedicated application referred to as a "patient app" or a web browser that interacts with a website provided by the health or home care provider. Alternatively, the sensor 210 and the inhaler 100 communicate with the patient computing device 420 via a local wired or wireless network (not shown) based on a protocol such as Bluetooth. The system 400 may include other inhalers (not shown) associated with respective patients who also have respective associated computing devices and associated HCP servers (possibly shared with other patients). All the patients/inhaler users in the system 400 may be managed by the data server 412.

As explained above, the data from the sensor 210 may be correlated with the application of drug doses from the inhaler 100. Additional data from the sensor 210 and the inhaler 100 may be collected by the computing device 420 to track the effectiveness of the drug and the technique of the patient in applying the drug as explained above in relation to an analysis module 454. Such data may be transmitted by either the inhaler 100 or the computing device 420 to the data server 412. The analysis module 454 may provide analysis of the collected data from the routine in FIGS. 3A-3B such as determining effectiveness of the drug, tracking dosages taken by individual patients such as the patient 410, or determining proper technique in use of the inhaler by individual patients.

In this example, the inhaler 100 is configured to transmit the physiological data from applying a drug dose to the patient computing device 420 via a wireless protocol, which receives the data as part of the patient program 440. The patient computing device 420 then transmits the physiological data to the data server 412 according to pull or push model. The data server 412 may receive the physiological data from the computing device 420 according to a "pull" model whereby the computing device 420 transmits the physiological data in response to a query from the data server 412. Alternatively, the data server 412 may receive the physiological data according to a "push" model whereby the computing device 420 transmits the physiological data to the data server 412 as soon as it is available after a dose is administered from the inhaler. As explained above, the data server 412 may implement the rules engine 230 shown in FIG. 2. Further, the data server 412 may access databases such as the database 240 to store collected and analyzed data.

Data received from the patient computing device 420 is stored and indexed by the data server 412 so as to be uniquely associated with the inhaler 100 and therefore distinguishable from physiological data collected from any other inhalers in the system 400. In this regard, although only one inhaler is illustrated in FIG. 4 for ease of explanation, the system 400 may include multiple inhalers. The data server 412 may be configured to calculate summary data for each dose application from the data received from the inhaler 100. The data server 412 may also be configured to receive data from the patient computing device 420 including data entered by the patient 410, behavioral data about the patient, or dose/summary data.

The EMR server 414 contains electronic medical records (EMRs), both specific to the patient 410 and generic to a larger population of patients with similar disorders to the patient 410. An EMR, sometimes referred to as an electronic health record (EHR), typically contains a medical history of a patient including previous conditions, treatments, co-morbidities, and current status. The EMR server 414 may be located, for example, at a hospital where the patient 410 has previously received treatment. The EMR server 414 is configured to transmit EMR data to the data server 412, possibly in response to a query received from the data server 412.

In this example, the HCP server 416 is associated with the health/home care provider (which may be an individual health care professional or an organization) that is responsible for the patient's respiratory therapy. An HCP may also be referred to as a DME or HME (domestic/home medical equipment provider). The HCP server 416 may host a process 452 that is described in more detail below. One function of the HCP server process 452 is to transmit data relating to the patient 410 to the data server 412, possibly in response to a query received from the data server 412.

In some implementations, the data server 412 is configured to communicate with the HCP server 416 to trigger notifications or action recommendations to an agent of the HCP such as a nurse, or to support reporting of various kinds. Details of actions carried out are stored by the data server 412 as part of the engagement data. The HCP server 416 hosts an HCP server process 452 that communicates with the analysis module 454 and the patient program 440.

For example, the HCP server process 452 may include the ability to monitor the patient user of the inhaler in accordance with compliance rules that specify the required inhaler usage over a compliance period, such as 30 days, in terms of a minimum number of doses, such as four times, for some minimum number of days, e.g. 21 days, within the compliance period. The summary data post-processing may determine whether the most recent time period is a compliant session by comparing the usage time with the minimum duration from the compliance rule. The results of such post-processing are referred to as "compliance data." Such compliance data may be used by a health care provider to tailor therapy that may include the inhaler and other mechanisms. Other actors such as payors may use the compliance data to determine whether reimbursement may be made to a patient. The HCP server process 452 may have other health care functions such as determining overall use of drugs based on collection of data from numerous patients. For example, health care organizations may run analysis algorithms to determine correlations between populations of patients using their drugs effectively and reduced hospitalization rates. Another example is determination of physiological patterns of pre- and post-drug use that indicate if a is at risk of imminent rehospitalization. Another example is an analysis of the effectiveness of different drug brands (but same drug type) in managing patient health.

As may be appreciated data in the data server 412, EMR server 414 and HCP server 416 is generally confidential data in relation to the patient 410. Typically, the patient 410 must provide permission to send the confidential data to another party. Such permissions may be required to transfer data between the servers 412, 414 and 416 if such servers are operated by different entities.

The analysis module 454 may collect data from dosage application and the corresponding physiological data and may be used to determine a customized dosage for the individual user. Other stored data may be used to further tailor a dosage. The customized dosage may be therefore determined based on the physiology, disease type and activity specific to the user. The additional data may be stored in a database and be used by the routine in FIG. 3A-3B as part of the analysis module 454 to assist in personalized analysis of the data received from the use of the inhaler 100.

Figure 5A:
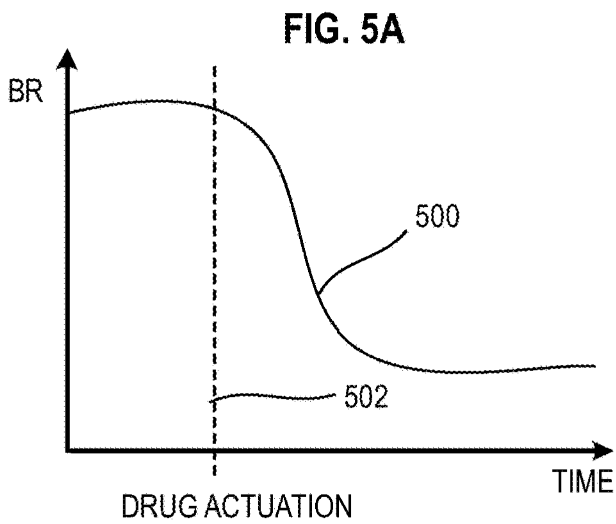
FIG. 5A is a graph of breath rate that may be used to determine the effectiveness of a drug dose using the system in FIG. 1A.

In this example, there are several techniques that may be used for measuring effectiveness of the inhaler dosage. First, effectiveness of asthma based drugs such as a bronchodilator may be measured based on breath rate or respiratory rate. Heartbeat or breath rate may be determined from a photoplethysmography sensor. FIG. 5A is a graph of breath rate that may be determined from the body sensor 210 in FIG. 2. FIG. 5A shows a plot 500 that represents the measured breath rate over time. A dashed line 502 represents the time the drug actuation occurs from activating the inhaler 100 in FIG. 1. As may be seen in FIG. 5A, the drug effectiveness may be evaluated by the decrease in breath rate after the drug actuation. A similar analysis may be used for plotting heart rate readings over time to determine the effectiveness of the drug.

Figure 5B:
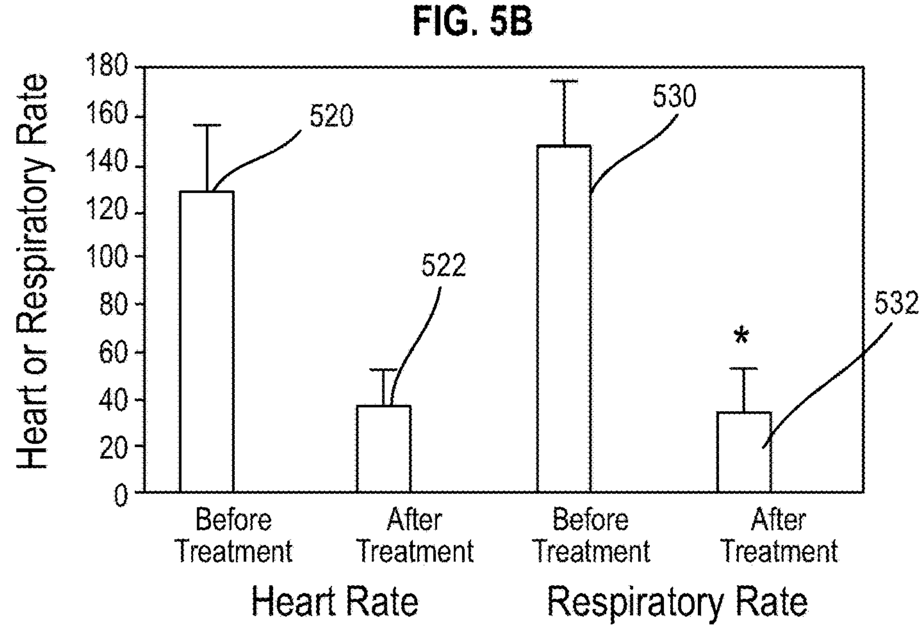
FIG. 5B is a bar graph of heart and respiratory rate that may be used to determine the effectiveness of a drug dose.

FIG. 5B is a graph that compares respiratory and heart rates before and after administration of albuterol through an inhaler such as the inhaler 100 in FIG. 1. FIG. 5B shows a bar 520 representing heart rate measurement before drug treatment and a bar 522 representing heart rate measurement after treatment. The lower heart rate represented by the bar 522 show the effectiveness of the drug treatment. Similarly, FIG. 5C also shows a bar 530 representing respiratory rate measurement before treatment and a bar 532 representing respiratory rate measurement after treatment. The lower respiratory rate represented by the bar 532 shows the effectiveness of the drug treatment.

Figure 5C:
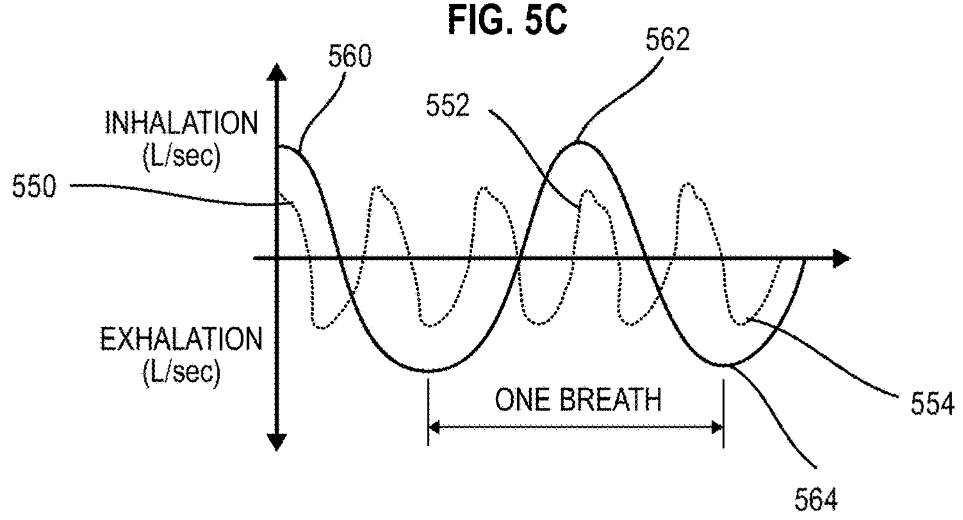
FIG. 5C is a graph of breath shape that may be used to determine the effectiveness of a drug dose.

Another technique may be to compare the breath shape before and after the administration of the drug. FIG. 5C is a graph of a breath curve 550 before drug dosage and a breath curve 560 after drug dosage. The curves show breath in liters per minute. In this example, the breath curve 550 includes an inhalation point 552 and an exhalation point 554. As may be seen in inhalation points 562 and exhalation points 564 on the breath curve 560, the breathing gets longer and deeper showing the effectiveness of the drug.

Another alternative may be a comparison of pulse rate data with the timing of the application of dosage from the inhaler 100. Another example, may be sensing CO2 or O2 from a patient's breath from an optical sensor or a capnograph and correlating the CO2 or O2 level with the effectiveness of the drug. Another example may be sensing CO2 or O2 from a sensor embedded in subcutaneous tissue.

Another alternative may be measuring effectiveness of inhaler dosage based on the measured pulse from a pulse oximeter sensor.

The flow diagram in FIGS. 3A-3B are representative of example machine readable instructions for collecting and analyzing data collected from the application of drug dosages by the inhaler 100 in FIG. 1. In this example, the machine readable instructions comprise an algorithm for execution by: (a) a processor; (b) a controller; and/or (c) one or more other suitable processing device(s). The algorithm may be embodied in software stored on tangible media such as flash memory, CD-ROM, floppy disk, hard drive, digital video (versatile) disk (DVD), or other memory devices. However, persons of ordinary skill in the art will readily appreciate that the entire algorithm and/or parts thereof can alternatively be executed by a device other than a processor and/or embodied in firmware or dedicated hardware in a well-known manner (e.g., it may be implemented by an application specific integrated circuit [ASIC], a programmable logic device [PLD], a field programmable logic device [FPLD], a field programmable gate array [FPGA], discrete logic, etc.). For example, any or all of the components of the interfaces can be implemented by software, hardware, and/or firmware. Also, some or all of the machine readable instructions represented by the flowcharts may be implemented manually. Further, although the example algorithm is described with reference to the flowchart illustrated in FIG. 3, persons of ordinary skill in the art will readily appreciate that many other methods of implementing the example machine readable instructions may alternatively be used. For example, the order of execution of the blocks may be changed, and/or some of the blocks described may be changed, eliminated, or combined.

As used in this application, the terms "component," "module," "system," or the like, generally refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller, as well as the controller, can be a component. One or more components may reside within a process and/or thread of execution, and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

The terminology used herein is for the purpose of describing particular embodiments only, and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Although the invention has been illustrated and described with respect to one or more implementations, equivalent alterations and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application. Thus, the breadth and scope of the present invention should not be limited by any of the above described embodiments. Rather, the scope of the invention should be defined in accordance with the following claims and their equivalents.

The invention claimed is:

1. An inhaler comprising:

an actuator to hold a drug container;

a dosing mechanism operable to aerate a dose from the drug container, the dosing mechanism providing the aerated dose to a user, the aerated dose configured to stimulate a physiological response of deepening a breath shape and slowing a breath rate of the user;

a sensor interface configured to be in communication with a physiological sensor, the physiological sensor configured to be attached to a user to sense physiological data from the user at a first base sampling rate, sense a physiological response to the dose, and send physiological data to the sensor interface; and a controller coupled to the sensor interface to increase the sample rate of the physiological sensor from the first base sampling rate to a second sampling rate for a predetermined period of time to collect the sensed physiological data from the user corresponding to the predetermined period of time after a time that the aerated dose is delivered to the user, and wherein the controller is operable to determine an effectiveness of the dose in deepening breath shape and slowing breath rate based on determining whether a plurality of breath shapes of the physiological data taken in the predetermined period of time is within range of a baseline physiological response of a deeper breath shape and a slower breath rate.

2. The inhaler of claim 1, further comprising a pressure sensor, wherein the controller is operable to determine an occurrence of an inhalation point of the user from an output of the pressure sensor relative to the provision of the dose.

3. The inhaler of claim 2, wherein the controller is operable to control the dosing mechanism to provide the aerated dose to the user at the inhalation point.

4. The inhaler of claim 1, further comprising one of an oxygen sensor, a heart rate sensor, or a carbon dioxide sensor, wherein the controller is operable to detect oxygenation in the user based on an output of the oxygen sensor, and determine an effectiveness of the dose based on the oxygenation in the user; or wherein the controller is operable to detect a heart rate in the user based on an output of the heart rate sensor, and determine an effectiveness of the dose based on the heart rate of the user; or wherein the controller is operable to detect breathing in the user based on an output of the carbon dioxide sensor, and operable to determine an effectiveness of the dose based on the carbon dioxide of a breath of the user.

5. The inhaler of claim 1, wherein the controller is operable to determine data associated with a breath of the user, the controller operable to analyze effectiveness of the dose based on the data associated with the breath of the user.

6. The inhaler of claim 1, wherein the controller is operable to determine data associated with a breath of the user and determine effectiveness of a technique applied by the user in activating the inhaler by comparing a breath shape derived from the data and a rule indicating dosage technique.

7. An inhaler based data collection system, the system comprising:

a physiological sensor configured to be coupled to a user to sense physiological data from the user at a first base sampling rate;

an inhaler mateable with a drug container, the inhaler including a dosing mechanism operable to aerate a dose from the drug container, the dosing mechanism providing the aerated dose to the user, the aerated dose configured to stimulate a physiological response of deepening a breath shape and slowing a breath rate of the user;

a sensor interface coupled to the physiological sensor to sense a response to the dose;

a controller coupled to the sensor interface to increase the sample rate of the physiological sensor from the first base sampling rate to a second sampling rate for a predetermined period of time to collect physiological data from the user corresponding to the predetermined period of time after a time that the aerated dose is delivered to the user, and a transceiver;

a data server to receive the collected physiological data from the transceiver; and an analysis module operable to determine an effectiveness of the dose based on the collected physiological data in deepening breath shape and slowing breath rate based on determining whether a plurality of breath shapes of the physiological data taken in the predetermined period of time is within range of a baseline physiological response of a deeper breath shape and a slower breath rate.

8. The data collection system of claim 7, wherein the analysis module is operable to send control data to the transceiver changing an amount of the aerated dose from the drug container in response to the effectiveness of the dose.

9. The data collection system of claim 7, wherein the analysis module is operable to determine a change in frequency to aerate the dose in response to the effectiveness of the dose.

10. The data collection system of claim 7, wherein the controller is operable to determine an occurrence of an inhalation point of the user from an output of the physiological sensor, and the controller correlates timing of the provision of the aerated dose to the inhalation point.

11. The data collection system of claim 10, wherein the analysis module is operable to determine the effectiveness of a technique applied by the user in activating the inhaler by comparing the inhalation point and a rule indicating inhaler technique.

12. The data collection system of claim 7, wherein the analysis module is operable to determine data associated with a breath of the user, and wherein the analysis module is operable to analyze the effectiveness of the dose based on the data associated with the breath of the user.

13. A dosage control unit for installation on an inhaler, the inhaler having an actuator holding a drug container containing a drug, a dosing mechanism coupled to the drug container to aerate a dose from the drug container, the dosing mechanism providing the aerated dose to a user, the dosage control unit comprising:

an interface attaching the dosage control unit to the inhaler;

a dosing sensor configured to detect the dosing mechanism aerating the dose, the aerated dose configured to stimulate a physiological response of deepening a breath shape and slowing a breath rate of the user;

a sensor interface configured to be in communication with a physiological sensor configured to be attached to the user of the inhaler, wherein the physiological sensor is configured to sense physiological data from the user at a first base sampling rate; and a controller coupled to the dosing sensor and the sensor interface, the controller operable to increase the sample rate of the physiological sensor from the first base sampling rate to a second sampling rate for a predetermined period of time to collect physiological data from the user corresponding to the predetermined period of time after a time that the aerated dose is delivered to the user, wherein the time that the aerated dose is delivered is determined from the dosing sensor, and wherein the controller is operable to determine an effectiveness of the dose in deepening breath shape and slowing breath rate based on determining whether a plurality of breath shapes of the physiological data taken in the predetermined period of time is within range of a baseline physiological response of a deeper breath shape and a slower breath rate.

14. The dosage control unit of claim 13, further comprising a pressure sensor, wherein the controller is operable to determine the occurrence of an inhalation point of the user from an output of the pressure sensor relative to the provision of the aerated dose, and the controller is further configured to control the dosing mechanism to provide the aerated dose to the user at the inhalation point.

15. The dosage control unit of claim 13, further comprising one of an oxygen sensor, a heart rate sensor, or a carbon dioxide sensor, wherein the controller is operable to detect oxygenation in the user based on an output of the oxygen sensor, and determine an effectiveness of the dose based on the oxygenation in the user; or wherein the controller is operable to detect a heart rate in the user based on an output of the heart rate sensor, and determine an effectiveness of the dose based on the heart rate of the user; or wherein the controller is operable to detect breathing in the user based on an output of the carbon dioxide sensor, and operable to determine an effectiveness of the dose based on the carbon dioxide of a breath of the user.

16. The dosage control unit of claim 13, wherein the controller is operable to determine data associated with a breath of the user, and wherein the controller is operable either to analyze effectiveness of the dose based on the data associated with the breath of the user; or determine effectiveness of a technique applied by the user in activating the inhaler by comparing a breath shape derived from the data associated with the breath of the user and a rule indicating dosage technique.

17. The dosage control unit of claim 13, further comprising a transceiver to transmit the collected physiological data to an external device, and to receive control data for the controller regulating the dosing mechanism to change a volume of the aerated dose provided by the dosing mechanism in response to analysis of the collected physiological data.

18. The dosage control unit of claim 17, wherein the external device is a mobile computing device associated with the user or a data server, and wherein the external device executes an application to analyze the collected physiological data to determine the control data.

* * * * *